US005560912A

United States Patent [19]
Neeman et al.

[11] Patent Number: 5,560,912
[45] Date of Patent: Oct. 1, 1996

[54] **METHOD FOR INHIBITING GROWTH OF *HELICOBACTER PYLORI***

[75] Inventors: Itzhak Neeman; Mina Tabak, both of Haifa; Robert Armon, Nesher, all of Israel

[73] Assignee: Technion Research & Development Foundation Ltd., Technion City, Israel

[21] Appl. No.: 266,013

[22] Filed: Jun. 27, 1994

[51] Int. Cl.$^6$ ............................. A61K 35/78; A61K 31/11
[52] U.S. Cl. .................. 424/195.1; 514/699; 514/926; 514/927
[58] Field of Search .................. 424/195.1; 514/703, 514/926, 927, 699

[56] References Cited

U.S. PATENT DOCUMENTS

| | | | |
|---|---|---|---|
| 4,202,877 | 5/1980 | Sato | 424/43 |
| 4,888,417 | 12/1989 | Shiraga et al. | 536/4.1 |

FOREIGN PATENT DOCUMENTS

| | | |
|---|---|---|
| 577481A1 | 1/1994 | European Pat. Off. |

OTHER PUBLICATIONS

Barry J. Marshall et al. "*Pyloric campylobacter* Infection And Gastroduodenal Disease". *Medical Journal of Australia,* Apr. 15, 1995, vol. 142, pp. 439–443.

Laura L. George et al. "Cure Of Duodenal Ulcer After Eradication Of *Helicobacter pylori*". *Medical Journal Of Australia,* Aug. 6, 1990, vol. 153, pp. 145–149.

Andrew H. Soll, "Pathogenesis Of Peptic Ulcer And Implications For Therapy". *The New England Journal Of Medicine,* Mar. 29, 1990, pp. 909–916.

Gabriele Geis et al., "Unusual Fatty Acid Substitution in Lipids and Lipopolysaccharides of *Helicobacter pylori*", Journal of Microbiology, May 1990, pp. 930–932.

K. Rosberg et al., "Adhesion of *Helicobacter pylori* to Human Gastric Mucosal Biopsy Specimens Cultivated in Vitro", Scand. J. Gastroenterol 1991, 26, pp. 1179–1187.

H. G. Desai et al., "Dental Plaque: A Permanent Reservoir of *Helicobacter pylori*?", Scand. J. Gastroenterol 1991, 26, pp. 1205–1208.

Laura L. Zaika, "Spices and Herbs: Their Antimicrobial Activity and Its Determination", Journal of Food Safety 9, 1988, pp. 97–118.

E. F. Steinmetz, Cotex Vegetabilis 1957.

*Primary Examiner*—John W. Rollins
*Attorney, Agent, or Firm*—Morgan & Finnegan

[57] ABSTRACT

The invention relates to the use of an organic extract of the plant Cinnamon or a chemical constituent present in said plant, to prepare a pharmaceutical composition useful to inhibit the growth of *Helicobacter pylori* and the urease activity of *Helicobacter pylori*. Most preferred chemical constituents are cinnamaldehyde and methoxycinnamaldehyde. The extract may be used either as a drink, with or without additional flavoring ingredients or transformed into a capsule. The invention also relates to in-vitro method for determininig the inhibition of urease activity of *Helicobacter pylori* using said organic extract of the plant or chemical constituents present in said plant.

7 Claims, 4 Drawing Sheets

METHOD FOR INHIBITING GROWTH OF *HELICOBACTER PYLORI*

The present invention relates to a new therapeutic application of particular chemical compounds or an extract of a plant containing them, to prepare a pharmaceutical composition useful to inhibit-the growth of pathogenic bacteria. More particularly, the invention relates to the use of said compounds or said extract, to prepare a pharmaceutical composition useful to inhibit the growth of *Helicobacter pylori* and urease activity of *Helicobacter pylori*.

BACKGROUND OF THE INVENTION

*Helicobacter pylori*, a bacteria isolated in 1982 from the stomach of patients with gastritis lesions and peptic ulceration, is a genus which formerly was related to Camphylobacter. *Helicobacter pylori* bacteria is the most common known cause of peptic ulcers and accounts for the majority of cases. It has been found in the antrum of more than 95% of patients with duodenal ulcers and in at least 75% of those with gastric ulcers. It is now generally accepted that this bacteria is associated with chronic and peptic ulcer disease and even possible with gastric cancer gastritis (Gabriele Geisel et al, Journal of Clinical Microbiology, May, 1990, 930-2). It also does produce urease in large amounts, which increases the pH in the microenvironment of the bacteria. *Helicobacter pylori* appears as a curved or S shaped gram-negative bacteria, its cell wall being smooth adhering closely to the cytoplasmic membrane. To-day, it is well recognized that the grade of *Helicobacter pylori* colonisation is associated with chronic gastritis and peptic ulceration. It is the general conclusion that the presence of *Helicobacter pylori* colonisation is of great importance in both the development and chronicity of peptic gastric ulcer disease. According to Marshall B. J. et al (Med.J.Austr. 1985, 439–443), more than 80% of cases of chronic gastritis and duodenal ulcer are associated with coexisting *Helicobacter pylori* infection and both have a relationship to the development of the ulcer disease. The routine treatment against *Helicobacter pylori*, is based on the use of bismuth subcitrate and antibiotics. However, this method does not eradicate *Helicobacter pylori* infection, and after a period of time the infection reoccurs.

Bismuth preparations were successfully used to combat various gastrointestinal disorders. The most commonly used are bismuth subsalicylate and colloidal bismuth subcitrate. Later on, combinations of bismuth salts with antibiotics, such as amoxycillin and metrodinazole, were also suggested. It was demonstrated that colloidal bismuth subcitrate improved dyspepsia by clearing the bacteria and not by any other effect of the drug on the gastrointestinal tract. To-day, it is considered that a triple therapy comprising:

(1) a bismuth compound;
(2) a nitroimidazole antibiotic; and
(3) tetracycline or amoxycillin, is effective in eradicating *Helicobacter pylori* infection in most patients (George L. L. et al, Med.J.Australian, 1990, 153, 145–9). However, as the authors pointed out, long-term follow-up is required in order to determine whether a recurrence of histologic gastritis symptoms will not appear. In any case, the authors pointed out that some diarrhea effects were reported due to *Clostridium difficile colitis*. On the other hand, some complaints of constipations were also reported after treatments with bismuth subcitrate alone.

According to a very recent report (Rosberg K. et al. Scand.J.Gastroenterol 1991, 26 p. 1179–1187) tests which were carried out on pigs show that a good correlation exists between adhesion of *Helicobacter pylori* to the gastric epithelium and gastritis, in-vivo and in-vitro infected specimens, using the same bacterial strains. This is a very important finding considering the fact that the adhesion of *Helicobacter pylori* to pig gastric mucosal specimen is quite similar to the human condition. In another recent paper (Desai H. G. et al. Scand J.Gastroenterol 1991, 26, 1205–8) it is reported that there is a relationship between the two reservoirs of *Helicobacter pylori*, i.e. dental plaque and the stomach. Using the Camphylobacter-like organism test, *Helicobacter pylori* was detected in dental plaque and in gastric antral and body mucosa of a number of patients with dyspepsia. It was found that the density of *Helicobacter pylori* is heaviest in dental plaque and less in the body mucosa of the stomach. The treatment by the triple drug system (bismuth, nitroimidazole and amoxycillin) shows that the bacteria was eliminated from the gastric mucosa, in all the 24 patients treated, but persisted in dental plaque in all of them. The authors concluded that the dental plaque is a major reservoir of *Helicobacter pylori*, being greater in their number than in the stomach and may be responsible for the reoccurence of infection after cessation of therapy in the body mucosa of the stomach. However, there are many reports which mention that "patients treated with antibiotics had side effects". Indeed, two recent reports publishedbin The New Egland Journal of Medicine (Vol. 322, No. 13, p.909–915) concern the eradication of *Helicobacter pylori* bacteria and discuss the disadvantages of bismuth and antibiotics. The above brief review clearly illustrates the potential diseases imparted by the *Helicobacter pylori* and the various approaches suggested to combat this bacteria, which unfortunately have not been successful in meeting that need.

It is an object of the present invention to provide a chemical composition or pharmaceutical extract to inhibit the growth of *Helicobacter pylori* bacteria. It is another object of the present invention to provide a chemical compound or a pharmaceutical extract to inhibit the growth of *Helicobacter pylori* without utilizing any of the known drugs or antibiotics. It is yet another object of the present invention to provide a chemical compound or a pharmaceutical extract for inhibiting the growth of *Helicobacter pylori* bacteria, which does not impart any undesired effects.

BRIEF DESCRIPTION OF THE INVENTION

The invention relates to the use of cinnamaldehyde or methoxycinnamaldehyde or an organic extract solution of the plant Cinnamon to prepare a pharmaceutical composition useful to inhibit the growth of *Helicobacter pylori* (hereafter referred to *H.pylori*) in a host containing same, in an amount which is sufficient to inhibit said growth. It was also found, that the above treatment is also useful to inhibit the activity of urease *H.pylori* both with the whole cells and the enzyme.

DETAILED DESCRIPTION OF THE INVENTION AND FIGURES

According to a first aspect, the invention relates to the use of an organic extract of the plant Cinnamon to prepare a pharmaceutical composition useful to inhibit the growth of *H.pylori* in a host containing same. The above composition which is administered to the host contains the cinnamaldehyde or methoxycinnamaldehyde or an organic extract solution of the plant Cinnamon, being in an amount that is sufficient to inhibit growth of the bacteria in the host. The solution of cinnamaldehyde or methoxycinnamaldehyde or said organic extract is provided either in the form of a drink or a capsule.

Cinnamon is a well known plant growing in many places. It was surprisingly found that many other plants which are known as medical plants and are quite similar to Cinnamon such as Camomile, Garlic, Olive rape, do not possess at all this property, or only to a very limited extent. Furthermore it should be pointed out that extracts of the above medical plants are mentioned in the literature to possess a medicinal property and are even suggested against disturbances in the digestion system.

In our European Patent Application No. 93.401638.7 it was described a pharmaceutical composition containing an aqueous or organic extract of the plant Thyme for the same purpose. It was surprisingly found according to the present invention, that only an organic extract of Cinnamon, is useful for preventing the growth of *H.pylori* bacteria in addition to the cinnamaldehyde and cinnamaldehyde which are the main constituents of the Cinnamon plant.

According to a second aspect, the invention relates to a method to inhibit in-vitro the growth of *H.pylori* bacteria by contacting said bacteria with an organic extract solution of the plant Cinnamon and said main constituents of the plant.

According to a third aspect, the invention relates to the use of the main chemical constituents present in the Cinnamon plant and most preferably cinnamaldehyde and methoxycinnamaldehyde, as a composition useful to inhibit the growth of *H.pylori* in a host containinig same, in an amount which is sufficient to inhibit said growth.

Figure 1:
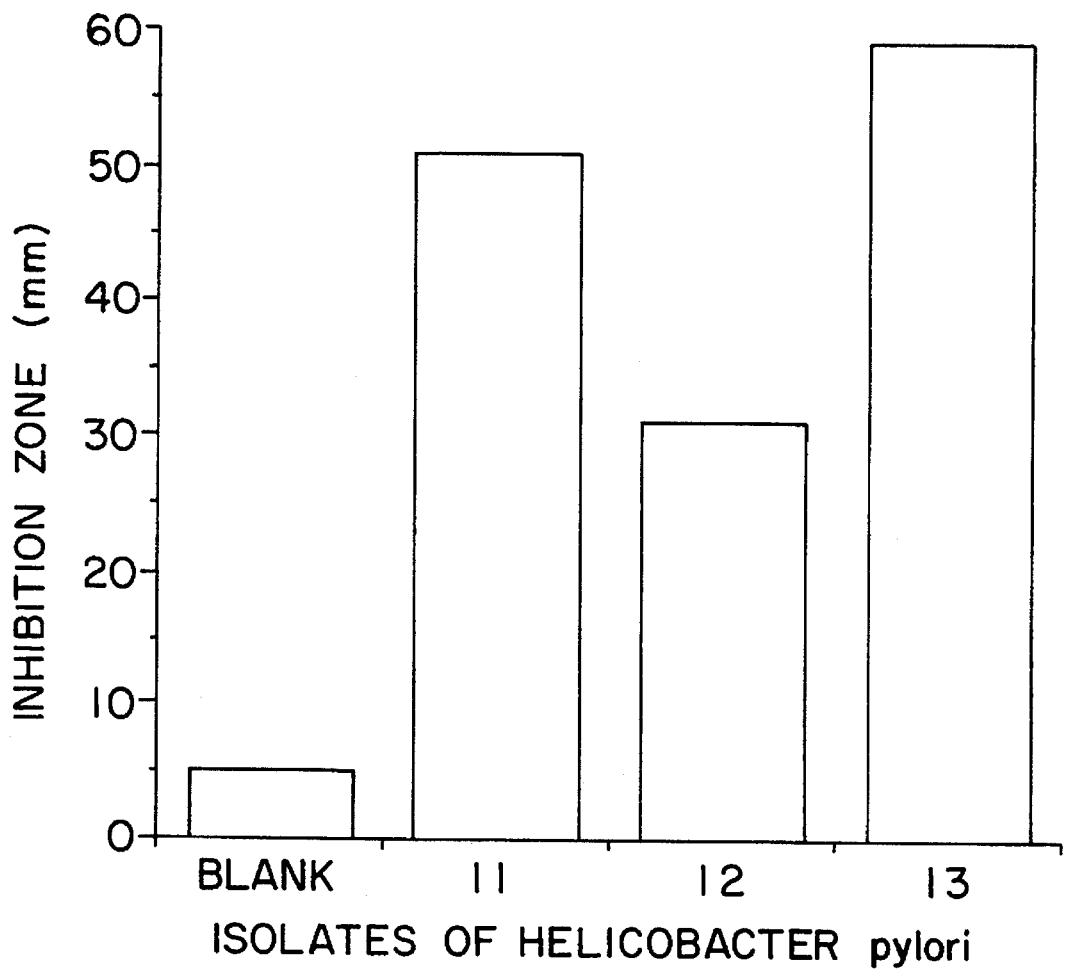
FIG. 1, shows the inhibition effect of alcohol Cinnamon extracts on three isolates of *H.pylori*.

The method was tested in-vitro on the various isolates of *Helicobacter pylori*, isolated from various patients, which were mentioned as :$I_1$, $I_2$ and $I_3$, and with all of them the same beneficial effect of growth inhibition was found. This appears in a clear manner from FIG. 1, where the inhibition effect of the alcohol extract of Cinnamon is illustrated towards three main isolates of *Helicobacter pylori*. This is an additional advantage over certain antibiotics which are not active to all these bacteria.

The inhibition activity of an organic extract of Cinnamon was tested on three isolates of *Helicobacter pylori* ($I_1$, $I_2$ and $I_3$) obtained from various patients and significant inhibition effects were noticed for the three isolates substantially at the same extent. On the other hand, it can be noticed in the Table 1, that some of these types of bacteria were not found to be affected by some known antibiotics substances.

TABLE 1

Behaviour of antibiotic substances to three isolates of *Helicobacter pylori*.

| Isolate of *H. pylori* | Sensitive to | Not affected by. |
|---|---|---|
| $I_1$ | ampicyllin | ceptarin |
| $I_2$ | nalidixic acid | erytromycin |
| $I_3$ | erytromycin | nalidixic acid |

As can be noticed, these isolates of bacteria were found not to be affected by some antibiotic substances,although they are known to be affected by others.

The inhibition effect was determined in-vitro, using the "Filter paper disc diffusion method" as described by Laura L. Zaika, (journal of Food Safety 9,1988,p.97–118). According to the method used, an extract of the plant was deposited on a small filter paper disc having a diameter of 0.5 cm and then placed in the center of a Petri plate containing agar growth medium inoculated with the test microorganism. The plate was incubated under microaerophilic conditions in anaerobic jars at 37° C. for 3 to 4 days and observed for microbial growth. If the extract of Cinnamon exerts antimicrobial activity, the microorganism will not grow in an area surrounding the filter paper disc. This clear area, defined as "zone of inhibition" was measured and recorded in mm. This method is well-known also for determining the activity of an antibiotic compound, by measuring the zone of inhibition arround a disc containing a sample of the antibacterial compound to be tested.

The assays used for the bacterial growth inhibition were as follows:

Two organic Cinnamon extracts, methylene chloride and ethanol in concentrations of 0.05 mg and 0.1 mg respectively were spotted on standard discs and placed on Egg Yolk Emulsion agar plate center which was previously layered with 0,1 ml of a bacterial suspension having a concentration of $10^7$ CFU ml.

Figure 2:
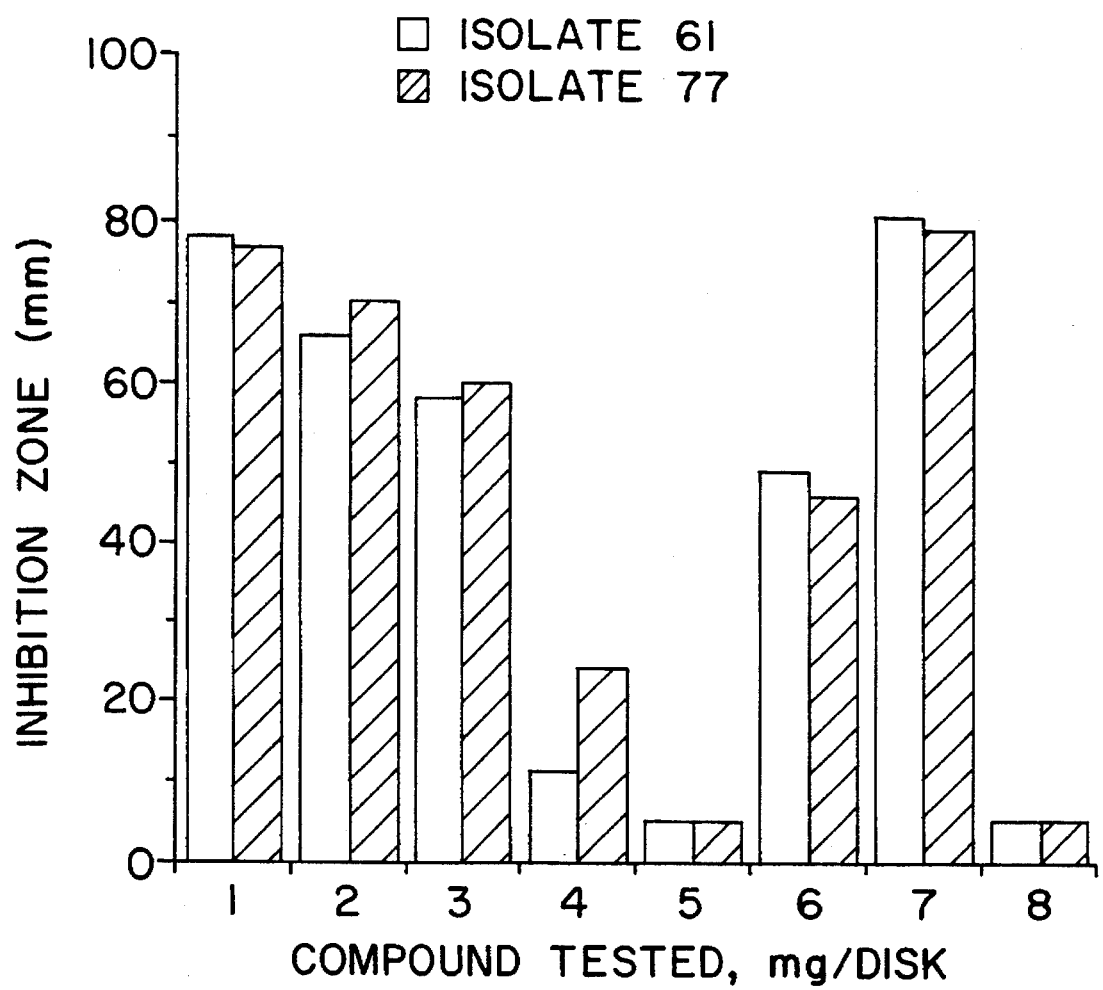
FIG. 2, illustrates the sensitivity of *H.pylori* to several antibiotics and Cinnamon plant extracts.

After the required incubation, the inhibition zone was recorded. In FIG. 2,there are presented the sensitivity of *Helicobacter pylori*, as determined by the inhibition diameter, using two organic extracts of Cinnamon (0,05 mg and 0.1 mg dry weight) compared with antibiotics: ampicillin (0.0. mg), tetracycline (0.03 mg), erythromycine (0.015 mg) nalidixic acid (0.03 mg), cotrimoxazole (0.025 mg). In these tests, two isolates of *H.pylori* were used.

It was surprisingly found that the inhibition of *H.pylori* growth is obtained only with an organic extract of Cinnamon and this effect is not obtained with organic extracts of other plants which are known by their medicinal potential activity. In the following Table 2, there are summarized the results of inhibition of said bacteria by some plants.

TABLE 2

Inhibition of *Helicobacter pylori* by various plant extracts.

| Plant extract type | Inhibition zone (in mm) | |
|---|---|---|
| | water extract | alcohol extract |
| Majorane | 22 | 18 |
| Inula | 5 | 12 |
| Rosemary | 10 | 8 |
| Licorice | 11 | 14 |
| Camomille | 5 | 5 |
| Cinnamon | 9 | 47 |

TABLE 2-continued

Inhibition of *Helicobacter pylori* by various plant extracts.

| Plant extract type | Inhibition zone (in mm) | |
|---|---|---|
| | water extract | alcohol extract |
| Laurel | 8 | 8 |
| Melissa | 18 | 14 |
| Thyme | 24 | 19 |
| Sage | 10 | 9 |
| Garlic | 5 | 7 |

As appears from the above Table, in none of the extracts of the plants other than Cinnamon, there is a significant inhibition of the bacteria. It can also be noticed, that only with an organic extract of Cinnamon, this inhibition exists, being much higher than that resulted with an aqueous extract. Also it clearly appears, that the inhibition zone of an aqueous extract of this plant is quite similar to the other aqueous and organic extracts of plants without possessing this activity.

The solvent used for the extraction of Cinnamon may be selected from a polar or non-polar solvent such as: ethanol, methylene dichloride, petrol ether, etc. In particular suitable will be the ethanol extract which can be taken as a drink, with or without any additional flavouring ingredients, added in order to improve the taste. When the solvent used is methylene dichloride or petroleum ether, it is suggested to evaporate all the solvent from the extract and subsequently to extract the dry matter by ethanol.

In the following Table 3, there are summarized the results on the inhibition of *H.pylori* growth, obtained by various concentrations of two Cinnamon extracts: Extract 1 (methylene chloride and after its removal add-adding ethanol) and Extract 2 (ethanol).

The tests were carried out on Egg Yolk Emulsion agar plate, the Cinnamon concentrations on disk were in the range of 12 mg to 800 mg.

TABLE 3

Inhibition of *Helicobacter pylori* growth by various concentrations of two Cinnamon extracts.

| Concentration (µg) | Inhibition Zone (mm) | |
|---|---|---|
| | Extract 1 | Extract 2 |
| 12 | 20 | 0 |
| 25 | 41 | 0 |
| 50 | 71 | 0 |
| 100 | 80 | 19 |
| 200 | >90* | 49 |
| 400 | >90* | 63 |
| 800 | >90* | 90 |

*indicates that a substantial complete inhibition occurred.

As appears from the above Table methylene extract with a concentration of 100 µg and above provides a complete inhibition of *H.pylori*.

Figure 3:
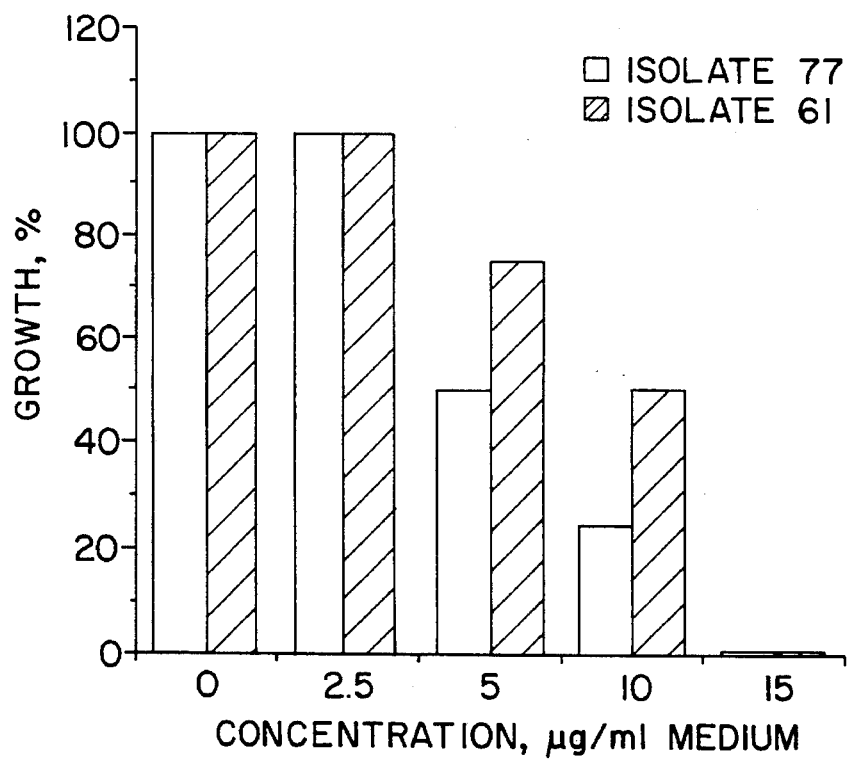
FIG. 3, illustrates the growth of *H.pylori* on Egg Yolk Emulsion agar with an organic extract of Cinnamon.
Figure 4:
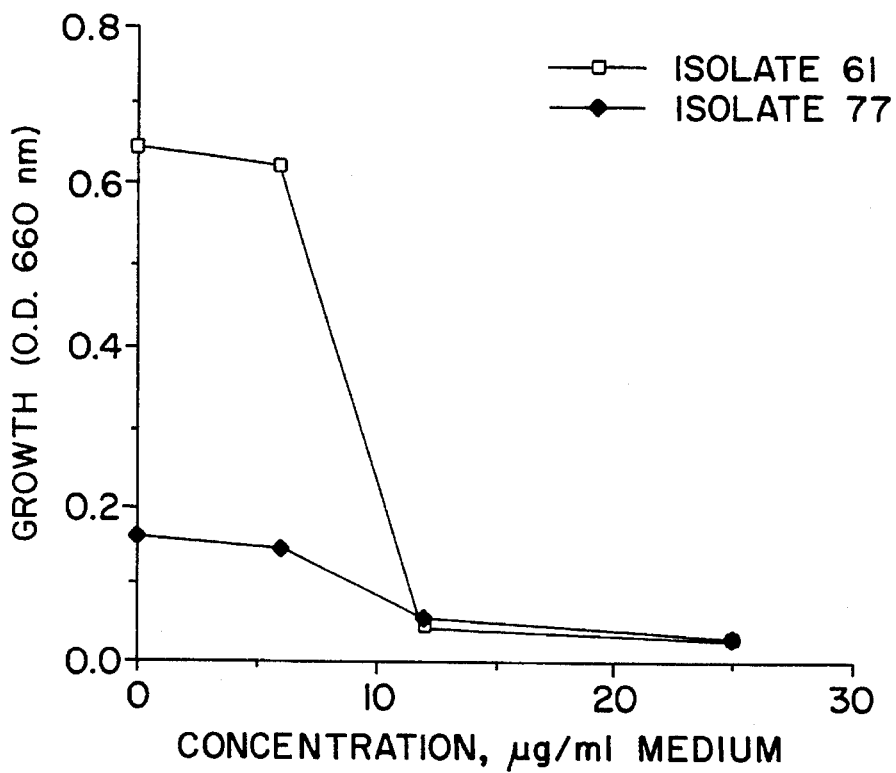
FIG. 4, illustrates the growth of two isolates of *H.pylori* in liquid medium with an organic extract of Cinnamon.

A Cinnamon extract was incorporated in a growth medium consisting of a solid form, Egg Yolk Emulsion agar, and a liquid form, Brain Heart Infusion Broth (BHIB) with 10% Fetal Calf Serum (FCS). The Minimal Inhibitory Concentration (MIC) for different isolates was 0.005 mg, while in the range of 0.015 to 0.05 mg, a complete ihibition was achieved. This appears in a clear manner from the attached FIGS. 3 and 4. One may also conceive to prepare the Cinnamon dry plant pressed in the form of a capsule, which also will impart the same inhibition diameter effect.

As mentioned above, instead of using an organic extract of Cinnamon plant, it was found that the main constituent of this plant, cinnamaldehyde and to a smaller extent methoxycinnamaldehyde, are producing also a significant inhibition of the *H.pylori* growth. The results obtained with some main constituents, are presented in the following Table 4.

TABLE 4

Inhibition of *H. pylori* growth by some of the main chemical constituents of Cinnamon plant.

| Chemical constituent | Concentration (mg/disk) | Inhibition zone (mm) |
|---|---|---|
| Cinnamaldehyde | 0.05 | 45 |
| " | 0.1 | 60 |
| " | 0.2 | >90* |
| Methoxycinnamaldehyde | 0.2 | 44 |
| " | 0.4 | 57 |
| " | 0.6 | 68 |
| Terpinen-4-ol | 2.0 | 22 |
| Alpha-pinene | 2.0 | 18 |
| Alpha-terpinene | 2.0 | 17 |
| Benzyl-benzoate | 2.0 | 17 |
| Cinnamic alcohol | 0.2 | 12 |
| " | 0.4 | 20 |

(* indicates that a substantial complete inhibition occurred).

As appears from the results of the inhibition zones as shown above, only the cinnamaldehyde even with a concentration of 0.2 mg/disk, produces a substantial complete inhibition. Methoxycinnamaldehyde also has a beneficial effect on the inhibition but with a higher concentration. Some other chemical constituents, such as cinnamic alcohol, or alpha-terpinene, produce only a lower inhibition zone even with a much higher concentration.

Another factor involved in the pathogenic mechanism of the bacteria, is urease of *Helicobacter pylori*. As known, the hydrolysis of urea and formation of ammonia enables the bacteria to resist the acidity which prevails in the stomach. The urease of *Helicobacter pylori* is well-known as a pathogenic factor and therefore its inhibition is indeed a long-felt need. There are known several chemicals which are described in the literature to possess an inhibition effect against urease of *Helicobacter pylori*. Among these chemicals the following reagents can be mentioned: aceto-hydroxamic acid, hydroxyurea, ethylene diamine tetraacetic acid and Lysine hydroxamate, none of them being present in the Cinnamon plant.

The organic extracts of Cinnamon were also found to be useful to possess the ability for inhibition of the activity of urease *Helicobacter pylori*, both with the whole cells and the enzyme. Even an alcoholic extract of 3.8 mg/ml Cinnamon, was found to inhibit up to 52.6% of increase activity of whole bacterial cells and at the same extent of bacterial lysate. This was determined using a modified method of Conway as follows: The reaction mixture contained:

2.0 ml of phosphate buffer (3 mM), pH = 6.8;

0.4 ml of urea (330 mM), and 0.1 ml of a suspension of whole cells ($10^7$ CFU/ml), or a solution of enzyme (special activity 483 µg $NH_4$/min/mg protein)

Cinnamon extracts were added to the reaction mixture at different concentrations. The reaction was continued for 30 minutes. After the addition of a saturated solution of potassium carbonate, the ammonia evolved was absorbed by boric acid and finally detected according to the method using the Bertholet reaction.

TABLE 5

Inhibition of *Helicobacter pylori* urease by Cinnamon extracts.

| Concentration of extracts in reaction mixture mg/ml | Urease activity (%). | |
|---|---|---|
| | Whole cells | Enzyme |
| 0.00 | 100.00 | 100.00 |
| 1.9 | | 7.90 |
| 3.8 | 52.6 | 5.99 |
| 7.6 | 41.36 | |
| 11.4 | | 5.42 |
| 15.2 | 30.92 | |
| 22.8 | 22.17 | |
| 38.0 | 8.00 | |

Figure 5:
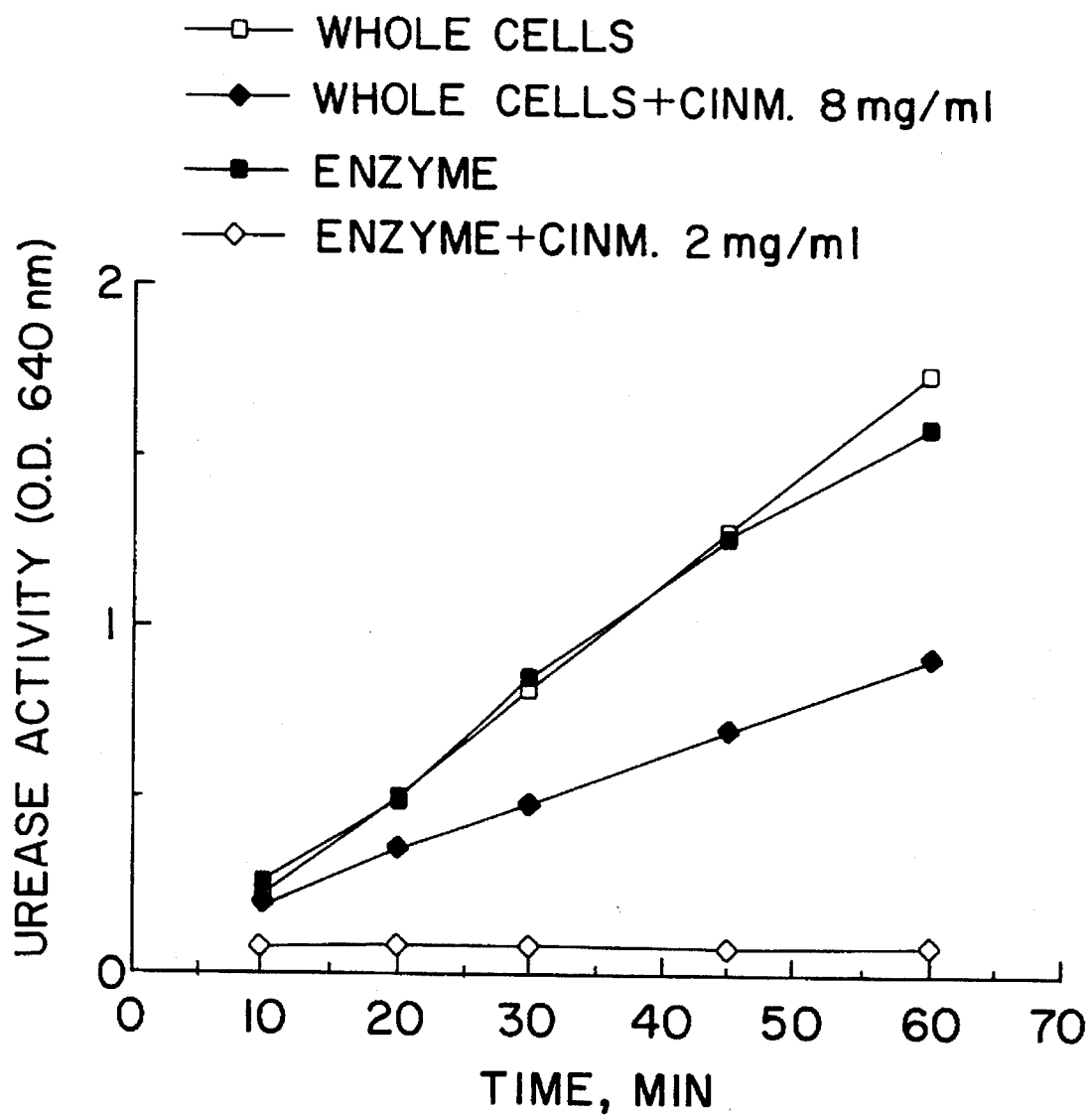
FIG. 5, illustrates the inihibition kinetics of *H.pylori* urease with whole cells and enzyme by an alcohol extract of Cinnamon.

In the attached FIG. 5, there are presented the graphs of inhibition kinetics of *H.pylori* urease, with whole cells and enzyme by an alcohol extract of Cinnamon.

Cinnamon extracts were added to the reaction mixture in concentrations of 8 mg/ml for whole cells and 2 mg/ml for the enzyme solution (on dry substance). The reaction time as 60 minutes. After the addition of a saturated solution of potassium carbonate, ammonia was absorbed by a solution of boric acid and detected according to Bertholet reaction. As can be observed, it clearly appears that the alcohol extract of Cinnamon imparts a much higher inhibition for enzyme than that corresponding to the whole cells.

We claim:

1. A pharmaceutical composition useful for inhibiting the growth of *Helicobacter pylori* in a host containing same, said composition comprising an effective amount of an organic extract of the plant Cinnamon and main chemical constituents present in said plant, selected from the group consisting of cinnamaldehyde, methoxycinnamaldehyde and mixtures thereof, said amount being a concentration of at least 5 µg/ml and effective for inhibiting the growth of the bacteria in the host.

2. The composition of claim 1, wherein said concentration is between 5 µg/ml and 25 µg/ml.

3. A method of inhibiting the growth of *Helicobacter pylori* bacteria in a host containing same, which comprises administering to the host an organic extract of the plant Cinnamon selected from the group consisting of cinnamaldehyde, methoxycinnamaldehyde and mixtures thereof, the extract of the plant Cinnamon being present in an amount that is sufficient to inhibit growth of the bacteria in the host.

4. The method of claim 3, wherein said extract is administered orally.

5. The method of claim 4, wherein said extract is administered in the form of a drink solution.

6. The method of claim 5, wherein additional flavoring ingredients are added in order to impart a desired taste to said drink solution.

7. The method of claim 3, wherein said extract solution is administered in the form of a capsule.

* * * * *